United States Patent [19]

Svegander et al.

[11] Patent Number: 4,816,760
[45] Date of Patent: Mar. 28, 1989

[54] METHOD AND APPARATUS FOR DETECTING THE POSITION OF AN EDGE OF A TEST PIECE

[75] Inventors: Lennart Svegander; Bengt Törnblom, Both of Västerås, Sweden

[73] Assignee: Asea AB & Törnbloms Kvalitetskontroll AB, Västerås, Sweden

[21] Appl. No.: 917,075

[22] Filed: Oct. 8, 1986

[30] Foreign Application Priority Data

Oct. 18, 1985 [SE] Sweden ................. 8504913

[51] Int. Cl.$^4$ ............... G01B 7/14; G01N 27/72; G01R 33/12
[52] U.S. Cl. ................... 324/207; 324/226; 324/232
[58] Field of Search ........... 324/225, 226, 232, 234, 324/236-243, 227, 207, 208; 364/563; 901/9, 46

[56] References Cited

U.S. PATENT DOCUMENTS 3,311,819  3/1967  Miller .................. 324/226
3,311,820  3/1967  Johnson ................ 324/226
4,019,131  4/1977  Yamada et al. ......... 324/229

FOREIGN PATENT DOCUMENTS 0101914  7/1983  European Pat. Off. .

Primary Examiner—Reinhard J. Eisenzopf
Assistant Examiner—Walter E. Snow
Attorney, Agent, or Firm—Watson, Cole, Grindle & Watson

[57] ABSTRACT

A method and apparatus for use with a measuring and-/or control device having at least one sensor based on eddy current induction and movable over a test piece and supplied with at least two carrier frequency signals. A determination is made on one of the carrier frequency signals with respect to those signal changes obtained at the transistion from measuring against the test piece to measuring against essentially empty space. When such signal changes occur an edge signal is generated which indicates that the measuring and/or control device has passed over an edge of the test piece.

10 Claims, 4 Drawing Sheets

METHOD AND APPARATUS FOR DETECTING THE POSITION OF AN EDGE OF A TEST PIECE

BACKGROUND OF THE INVENTION

1. Field of the Invention

The present invention relates to a method and apparatus for use in a measuring and/or control device with a sensor based on eddy current induction moving over a test piece, and particularly to such apparatus for determining the edges of the test piece.

2. Related Art

The invention has been developed particularly for application in conjunction with measuring apparatus of the kind which incorporate proximity sensors based on eddy current induction and intended for measuring cracks present in metal objects having relatively broad surfaces, such as metal sheet, cylinders or the like. One field in which the invention finds particular applicability is that of continuous casting, in which the solidifying steel ingot is advanced in a continuous length. The continuous metal ingot is then cut into billets, which are subsequently treated by rolling or like processes. Cracks frequenty occur in the cast material. Consequently, a crack detecting apparatus incorporating proximity sensors based on eddy current induction has been developed for detecting the presence of surface cracks in the material. This apparatus is described and illustrated in Swedish Patent Applications Nos. 7613708-2, 8206678-8 and 8302738-3.

The cracks are located by passing a sensor head provided with eddy current inducing proximity sensors across the surface of a test piece, e.g. the continuous ingot, to be examined for cracks. The test piece is advanced continuously in a conventional manner, essentially transversely to the sweep direction of the head.

The width of continuous cast test pieces can vary considerably, and may even vary during one and the same casting operation. One problem which often occurs in continuous casting processes is that of continuously defining the width of the casting, e.g. the ingot, in a reliable manner. Hitherto, no apparatus which meets with complete satisfaction has been proposed for measuring or defining the width of castings, particularly hot continuous cast ingots.

One problem encountered with crack measuring apparatus using proximity sensors based on eddy current inducement is one of controlling the turning point of a sensor sweep, or scan, with the aid of the momentary location of an edge of a test piece. It is true that separate edge detecting units can be placed in the close proximity of the position at which the sensor passes out over the edge of the test piece during a sweep or scan, but the use of additional measuring systems is always to be avoided as far as possible, since additional systems increase costs, complicate the technical solution, and require space.

SUMMARY OF THE INVENTION

The aforesaid problems are avoided by means of the method and apparatus according to the present invention.

The edge signal, at least from one side of the test piece, can then also be used as a starting point for calculating the location of the cracks detected in the test piece in that case when the proximity sensor is used both as an edge detector and as a crack detector. This results in particularly precise positional determination of the locations of the edges and the cracks, since the work is carried out with one and the same sensor.

BRIEF DESCRIPTION OF THE DRAWINGS

The invention will now be described in more detail with reference to the accompanying drawings, in which.

DETAILED DESCRIPTION

Figure 1:
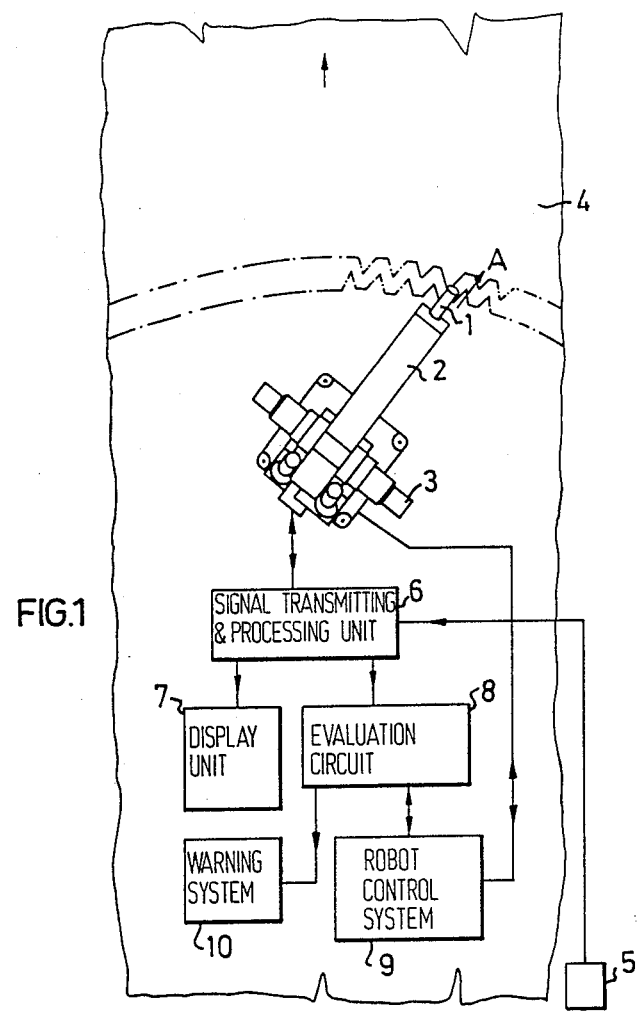
FIG. 1 is a principle illustration of a first conceivable embodiment of a system for continuously detecting the presence of cracks in a continuously cast test piece and establishing the location of the cracks therein, with the aid of edge detection in accordance with the invention.

The FIG. 1 embodiment of apparatus for detecting continuously the presence of cracks in a continuously cast test piece comprises a proximity sensor arrangement which may incorporate one or more proximity sensors mounted in a head placed on one end of an arm 2 of a pivotable or swingable robot 2. The head is positioned at a substantially constant, regulated distance from one surface of a forwardly moving, still flowing continuously cast test piece 4. The robot 3 is swung from one side of the test piece 4 to the other by drive means intended herefor. It will be understood, however, that a robot 3 may be positioned either beneath or adjacent one side of the test piece, or adjacent all sides thereof, depending on which of the surfaces of the test piece is to be examined for cracks. For the sake of simplicity, however, the following description will be made solely with reference to a measuring system which is located above the test piece.

The sensor head 1 on the arm 2 of the robot can be moved across the test piece in one continuous movement. However, since the sensor head is only able to cover a relatively small area of the test piece surface during said examination procedure it is preferable to arrange for the sensor arrangement to move on the sensor head 1, in the execution of a crack detecting sweep cycle, in a direction different to the sweep direction. Accordingly, in the embodiment illustrated in FIG. 1 the head 1 is driven reciprocatingly in the direction of the arrow A. The sensor arrangement moves across the test piece along a circular arc with superimposed transverse oscillatory movements. Since the process of edge detection carried out in accordance with the invention provides an extremely accurate result, and since the apparatus and equipment used herefor is capable of withstanding the troublesome environment in which the work is carried out, the apparatus according to the invention can also be used with great advantage solely for detecting the location of an edge of a test piece, i.e. without requiring the apparatus to detect the presence of cracks. In this case, of course, the sensor arrangement need not move transversely to the sweep direction.

The sensor arrangement co-acts with a signal transmitting and signal processing unit 6 which calculates the location of detected cracks in a transverse direction, with a starting point from the last detected position of an edge on one side of the test piece, and in a longitudinal direction with a starting point from the time at which the leading edge of the test piece was last located and also on the basis of the speed at which the test piece is advanced, this data being obtained through a sensor 5 incorporated in the continuous casting apparatus. The unit 6 presents this data on a display or presentation unit 7.

In accordance with the invention, a signal from the unit 6 is applied on a second output immediately a radical change occurs in the value of the measuring signal or signals, such as when no eddy currents are induced in the underlying material of the test piece or when the eddy currents decrease to a marked extent, which either indicates that the sensor arrangement has been moved inwardly or outwardly over the edge of the test piece 4, or that the test piece has located therein a crack of particular width and depth immediately beneath the sensor arrangement. This signal is transmitted to an evaluating circuit 8 which may optionally be constructed to carry out a so-called probability check on the signal, by checking the rotational position of the robot arm, this position being indicated by a control circuit 9, which is normally incorporated in the robot but which for the sake of simplicity is shown separately, and which accepts the signal from the unit 6 as an edge marking if said rotational position lies outside pre-determined limits in one direction or the other.

If such is the case there is produced a signal which indicates that the edge has been reached. This signal is used in a number of ways, as described in more detail hereinafter.

The evaluating circuit 8 may be constructed such as to send a signal to an alarm or warning circuit 10 when said circuit 8 receives a signal from the unit 6 with the sensor arrangement located above the test piece 4.

Figure 2:
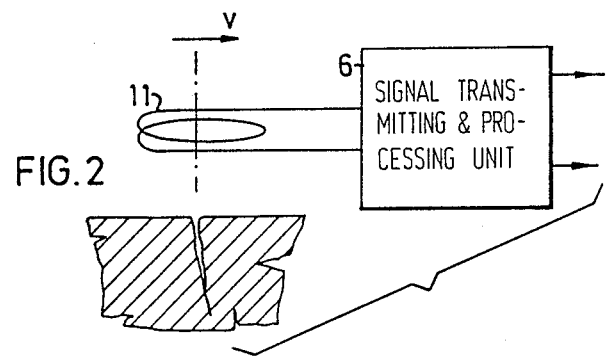
FIG. 2 illustrates an embodiment of a proximity sensor used in accordance with the invention.

FIG. 2 illustrates an embodiment of a suitable proximity sensor based on eddy current inducement, this proximity sensor being of the kind illustrated and described in U.S. Pat. No. 4,646,013. A coil 11 is supplied with alternating current from the signal transmitting and signal processing unit 6. The alternating current includes two mutually different components fL and fH. Eddy currents of corresponding frequency content are induced in the surface of the test piece, through the inductive coupling thereto. The voltage across the coil is detected and divided into its respective frequency components. The resultant signals are utilized for crack detection purposes. One of these signals, namely the signal having the higher frequency, is used for edge marking purposes, since this signal has a high so-called lift-off-dependency, i.e. is highly dependent on the distance of the sensor from the measured surface on the test piece.

Figure 3:
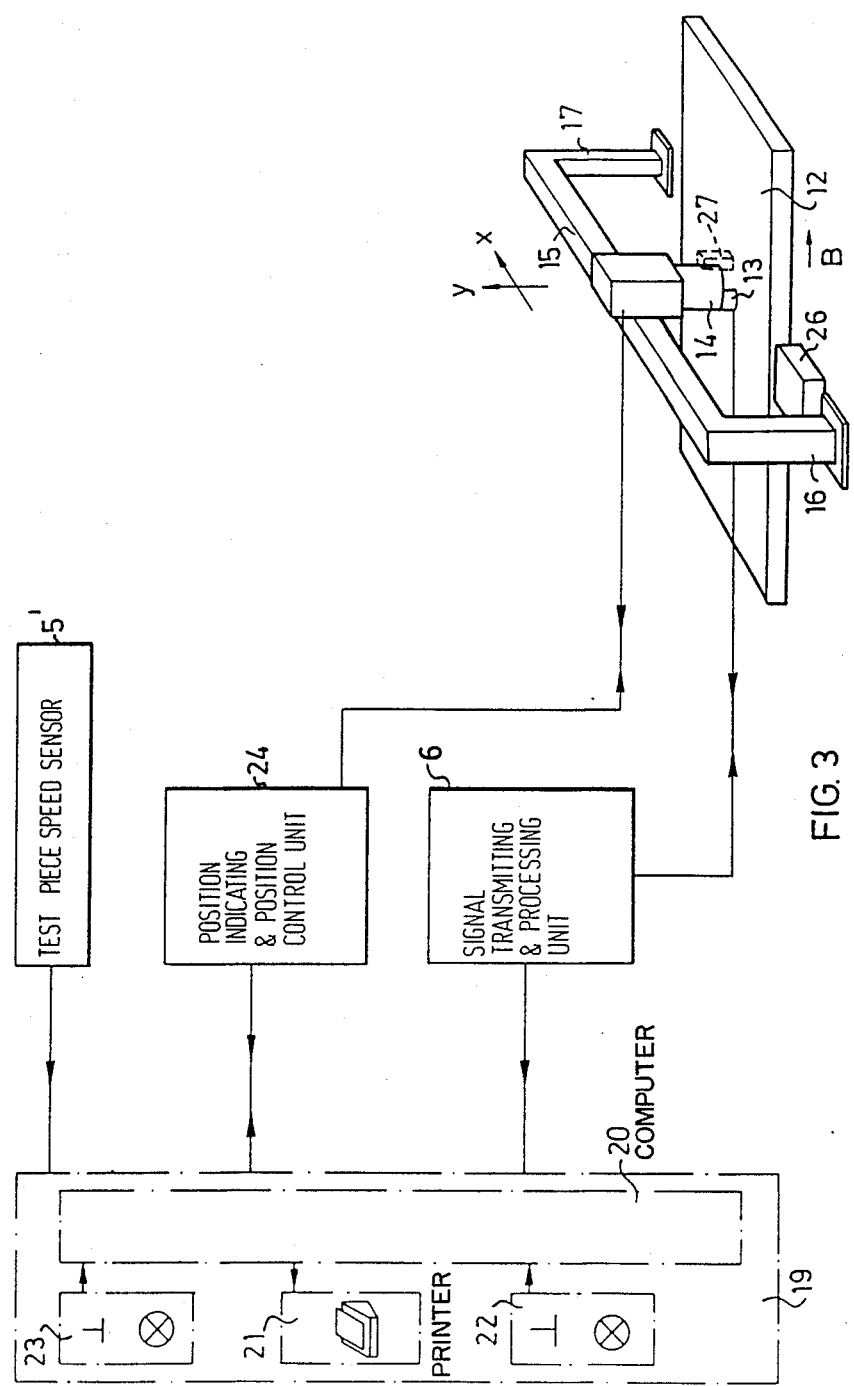
FIG. 3 is a principle illustration of a second conceivable embodiment of a system for continuously detecting the presence of cracks in a continuously cast test piece and for establishing the location of said cracks with the aid of edge detection in accordance with the invention.

FIG. 3 illustrates apparatus for localizing cracks, in which a transducer arrangement is moved across a test piece in a rotational movement pattern. The test piece, here referenced 12, moves forwards continuously in the direction of the arrow B. A sensor arrangement 13 is mounted for rotation on a sensor head 14, which incorporates a drive motor. The sensor head 14 is mounted for guided movement along a beam 15, which is placed on pillars 16, 17 and extends across the path travelled by the test piece. It will be understood that when the apparatus is used solely for edge detecting purposes the sensor need not rotate.

The signal transmitting and signal processing unit 6 feeds auxiliary signals to the sensor arrangement 13, as beforedescribed, and evaluates the signal or signals received from said sensor arrangement.

The unit 6 is connected in turn to a control and monitoring unit 19. The unit 19 incorporates a computer 20 or like device with peripheral equipment for presenting the results obtained, such as a printer 21 and/or an image screen or the like, a key-board 22 for manual insertion of data and/or some other type of data input unit 23.

Computer 20 is a mainframe computer such as "Masterpiece 200" as sold by ASEA, the Assignee of the subject application.

The unit 19 is also supplied with a signal from a positional indicating and positional control unit 24 operating in conjunction with the sensor arrangement. The unit 24 indicates continuously the position of the sensor arrangement 13 in relation to the test piece, both in the lateral direction (x) and the vertical direction (y), and initiates adjustment of the distance of the sensor arrangement from the opposing surface of the test piece, by actuating a height regulating device (not shown) in a manner to raise and lower the head 14. As indicated in the foregoing, the momentary forward speed of the test piece is also measured, with the aid of a sensor 5', and the result of the measurement is delivered to the computer 20, which calculates the distance through which the test piece has moved, on the basis of said speed. The unit 19 also controls the movement of the head 14 along the beam 15, in the manner illustrated in FIG. 4. This control procedure is also suitable for the embodiment illustrated in FIG. 1. The two vertical broken lines $K_1$ and $K_2$ represent the probable positions of the two edges of the test piece. These positions are calculated by the computer 20 and the mean value of the position of a detected edge during a given number (e.g. 10) of previously effected edge detecting procedures. It will be understood, however, that it is possible to use solely the latest detected positions, although the procedure in which a mean value is taken of a plurality of edge detections is to be preferred.

The sensor head 14 begins its journey across the test piece with at least a small part of the path travelled by the sensor arrangement located externally of the edge $K_1$. The sensor head is accelerated from a zero speed at $S_1$ to the intended speed of travel, reached at $S_2$, and maintains this intended speed until reaching the point referenced $S_3$, which lies at a distance from the edge $K_2$ such that the head 14 is able to decelerate to a far lower speed than the travelling speed reached at $S_4$, which lies slightly inwardly of the edge $K_2$, and is maintained at this lower speed until the edge $K_2$ is detected at $S_5$, whereafter the head is decelerated to zero speed at $S_6$. The head 14 is then held stationary at $S_6$ until the test piece has advanced through a pre-determined distance from, and including the moment at which the head 14 is caused to move over the test piece at $S_1$. The head 14 is then caused to move in the opposite direction across the test piece in a corresponding speed pattern $S'_1$–$S'_6$.

The reason for decelerating the speed of the sensor head to the lowest speed at $S_4$ and $S'_4$ respectively is because the sensor arrangement 13 shall pass slowly over respective edges, thereby enabling the location of said edges to be determined in a particularly precise manner.

The computer computes the edge signals from the signals obtained from the units 6 and 24 and, with a starting point from at least one of the edge signals, optionally also the position and extension of the detected cracks, using herefor the edge marking obtained at one edge. The width of the test piece is calculated with the aid of the edge signal obtained from the other edge. Preferably, at least two memory regions are reserved in the computer 20 for width calculation purposes. In this way, the width of the test piece is calculated continuously, and the results may be presented on a display or presentation unit 21. The unit 21 may optionally also incorporate a curve printer having two channels for visible display.

As beforementioned, the edge signals obtained as the sensor arrangement passes locations $S_5$ and $S'_5$ can be utilized for generating a stop signal effective for stopping movement of the head 14 along the beam 15. Alternatively, it is also possible to permit the head 14 to continue its outward movement subsequent to receiving said edge signal, through a distance corresponding, for example, to a single or double radius of the circle described by the sensor arrangement, or some like measurement.

Figure 5:
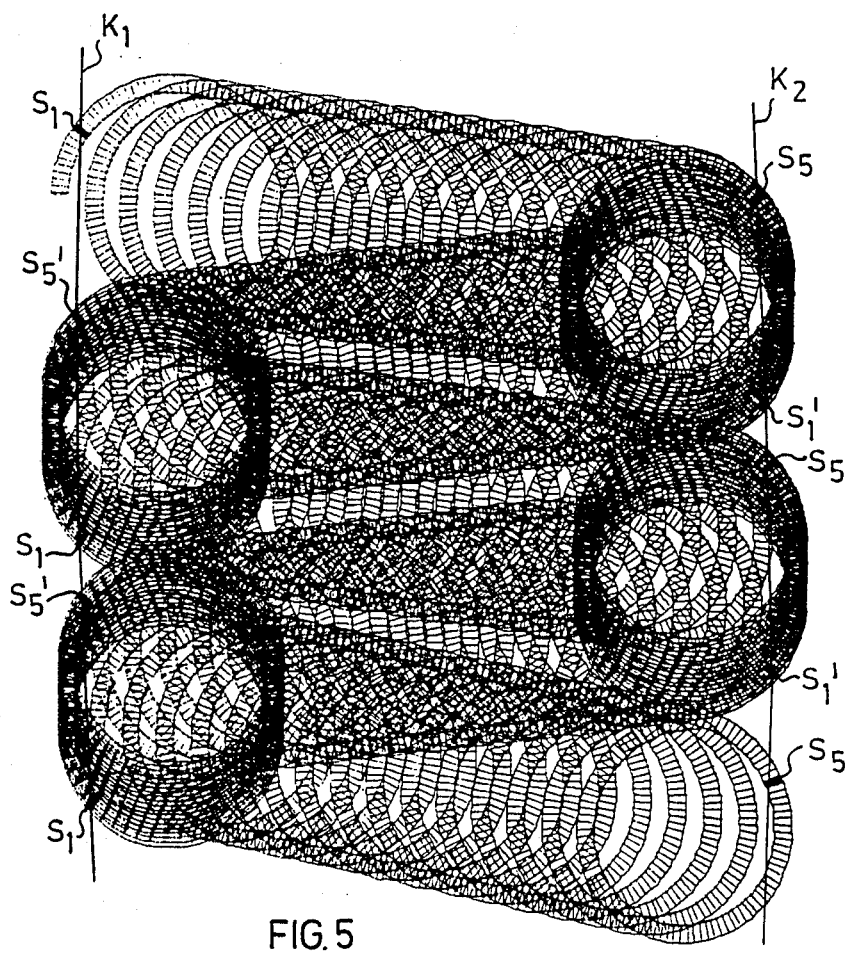
FIG. 5 illustrates embodiments of the patterns of movement executed by the sensor in FIG. 3 during its travel across the test piece.

FIG. 5 illustrates an example of the pattern of movement executed by the sensor arrangement 13 when the head 14 is passed backwards and forwards across the test piece a number of times on the beam 15.

The span capable of being covered by the actual sensor itself is solely equal to the breadth of the illustrated helically shaped, hatched band, although by rotating the sensor there is obtained with each pass over the test piece a covering band equal in width to the diameter of the circle described by said rotation. It will be understood that the loops or turns of the helix may lie closer together than those illustrated.

Figure 4:
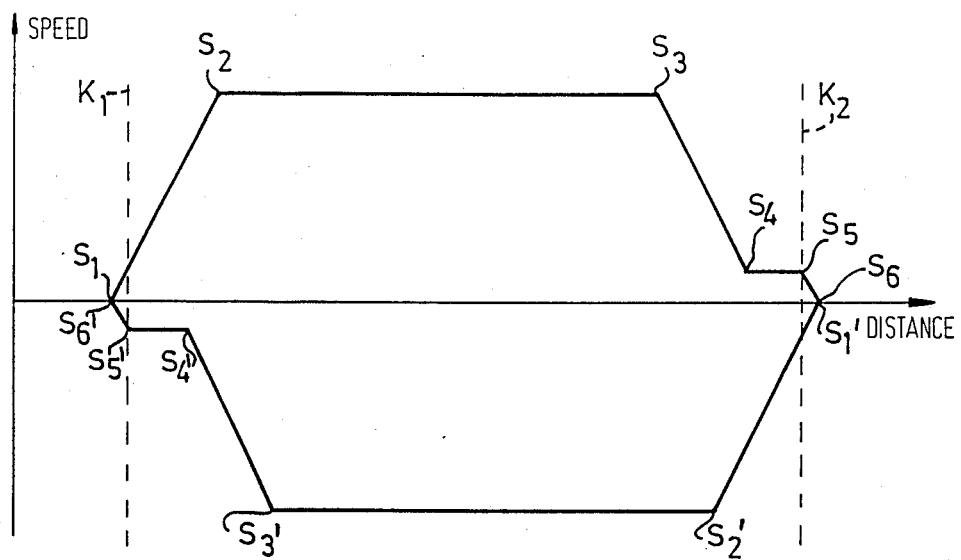
FIG. 4 is a diagram illustrating the speed at which the proximity sensor head travels across the test piece.

Since, when using the rotary sensor head 13, it is that part of the turn which lies closest the edge which shall be sensed, i.e. the outer part of the sensor head 14 located adjacent each edge, this being essential to accurate edge detection, the velocity diagram in FIG. 4 shall, in this case, be read so that the velocity in this close proximity of a relevant edge denotes the velocity of the outer part of the sensor head at said edge. This has been indicated in FIG. 5, by marking therein the edges $K_1$ and $K_2$ and the positions for $S_1$, $S_5$, $S'_1$ and $S'_5$.

It will be understood that the indication of the position of an edge of the test piece, carried out during each scanning cycle, need not necessarily be effected with the same sensor as that used for crack detection, but that, for example, a non-rotating sensor 27 may be mounted on the outside of the head 14. In this arrangement, the rotating sensor will pass beyond the test piece through a distance equivalent to one radius of rotation prior to the non-rotating sensor 27 indicating the location of said edge. If wishing to reduce the stationary edge time to the greatest possible extent when reaching the edge, the actual head 14 itself may also be arranged to rotate through at least one half revolution, and to be rotated so as to turn the non-rotatable sensor 27 towards the opposite edge prior to travel in the opposite direction.

We claim:

1. Apparatus in a measuring and/or control device having a sensor based on eddy current inductance and arranged to be moved across a test piece, said sensor is of a kind supplied with at least two carrier frequency signals, comprising:

an electric evaluating circuit for receiving the output signal from at least one of said sensor directly and indirectly derived from one of said input carrier frequency signals, said circuit reacting to given specific changes in the output signal taking place at the transition from measuring against the test piece to measuring against essentially empty space and/or vice versa, and, upon the occurrence of said signal changes, to apply an output signal to a control circuit for a drive means for movement of said sensor, indicating that said sensor has been moved out or in over the edge of the test piece, a circuit associated with said control circuit and is operative to indicate the position of said sensor, said position indicating circuit having an output connected to the evaluating circuit, and the evaluating circuit, upon the occurrence of a change in the output signal compares whether the position in question lies outside predetermined limits, outside of which an edge of the test piece is likely to be found, and to send an output signal to the control circuit when said position lies outside said predetermined limits.

2. An arrangement according to claim 1, wherein the evaluating circuit includes a memory which stores at least the latest obtained position in respect of the sensor positions upon the occurrence of an edge signal at each side of the test piece; and the evaluating circuit is arranged to calculate the width of the test piece subsequent to receiving each edge marking signal, said calculation being made on the basis of the positional values stored in the memory.

3. An arrangement according to claim 1, wherein the evaluating circuit has one memory which stores, in respect of each side of the test piece, at least one of the latest obtained position and a mean value of a given number of latest obtained positions in respect of the sensor position upon the occurrence of an edge signal; and means for controlling a sweep cycle causes a sensor head to sweep across the test piece up to a point located at a determined distance from the position stored in the memory of that edge which shall be passed in a prevailing sweep, and to lower the speed of the head to a speed which is much lower than the travel speed of the head, and to maintain the head at this lower speed until the edge signal is obtained, and then to lower the speed of the head to substantially zero.

4. Apparatus in a measuring and/or control device having a sensor based on eddy current inductance and arranged to be moved across a test piece, said sensor is of a kind supplied with at least two carrier frequency signals, comprising:

an electric evaluating circuit for receiving the output signal from at least one of said sensor directly and indirectly derived from one of said input carrier frequency signals, said circuit reacting to given specific changes in the output signal taking place at the transition from measuring against the test piece to measuring against essentially empty space and/or vice versa, and, upon the occurrence of said signal changes, to apply an output signal to a control circuit for a drive means for movement of said sensor, indicating that said sensor has been moved out or in over the edge of the test piece, the evaluating circuit has a memory which stores at least the latest obtained position in respect of the sensor positions upon the occurrence of an edge signal at each side of the test piece; and the evaluating circuit calculates the width of the test piece subsequent to receiving each edge marking signal, said calculation being made on the basis of the positional values stored in the memory.

5. Apparatus in a measuring and/or control device having a sensor based on eddy current inductance and arranged to be moved across a test piece, said sensor is of a kind supplied with at least two carrier frequency signals, comprising:

an electric evaluating circuit for receiving the output signal from at least one of said sensor directly and indirectly derived from one of said input carrier frequency signals, said circuit reacting to given specific changes in the output signal taking place at the transition from measuring against the test piece to measuring against essentially empty space and-/or vice versa, and, upon the occurrence of said signal changes, to apply an output signal to a control circuit for a drive means for movement of said sensor, indicating that said sensor has been moved out or in over the edge of the test piece, the evaluating circuit has one memory which stores, in respect of each side of the test piece, at least one of the latest obtained position and a mean value of a given number of latest obtained positions in respect of the sensor position upon the occurrence of an edge signal; and means for controlling a sweep cycle a sensor head to sweep across the test piece up to a point located at a determined distance from the position stored in the memory of that edge which shall be passed in a prevailing sweep, and to lower the speed of the head to a speed which is much lower than the travel speed of the head, and to maintain the head at this lower speed until the edge signal is obtained, and then to lower the speed of the head to substantially zero.

6. A method for the use of a measuring and/or control device having a sensor based on eddy current induction and moved over a test piece, comprising:

supplying the sensor with at least two carrier frequency signals;

determining from at least one of said carrier frequency signals whether signal changes are present indicating transfer from measuring against a test piece to measuring against essentially empty space or vice-versa;

producing an edge signal when detecting said signal changes indicating that said sensor has passed outwardly or inwardly over an edge of said test piece; and determining the position of said sensor upon the occurrence of said signal changes and determining whether said position is located within an area in which an edge of the test piece is likely to be found.

7. A method according to claim 6, further comprising passing at least one of the measuring and control device in a sweeping movement from one side of the test piece to the other; and storing the lateral positions at which edge signals occur, and calculating the width of the test piece continuously on the basis of said positions for each pair of edge signals, one on each side of the test piece.

8. A method for the use of a measuring and/or control device having a sensor based on eddy current induction and moved over a test piece, comprising:

supplying the sensor with at least two carrier frequency signals;

scanning said sensor from one side of the test piece to the other;

determining from at least one of said carrier frequency signals whether signal changes are present indicating transfer from measuring against a test piece to measuring against essentially empty space or vice-versa;

producing an edge signal when detecting said signal changes indicating that said sensor has passed outwardly or inwardly over an edge of said test piece;

storing the lateral positions at which edge signals occur; and calculating the width of the test piece continuously on the basis of said positions for each pair of edge signals, one on each side of the test piece.

9. A method according to claim 8, further comprising passing at least one of the measuring and control device in a sweeping movement from one side of the test piece to the other with a determined travel speed across the test piece for each sweep up to a determined distance from the expected position of said edge, at which position the speed of the device is lowered to a level considerably lower than said travel speed, so that said device passes said edge at the lower speed.

10. A method for the use of a measuring and/or control device having a sensor based on eddy current induction and moved over a test piece, comprising:

supplying the sensor with at least two carrier frequency signals;

determining from at least one of said carrier frequency signals whether signal changes are present indicating transfer from measuring against a test piece to measuring against essentially empty space or vice-versa;

producing an edge signal when detecting said signal changes indicating that said sensor has passed outwardly or inwardly over an edge of said test piece;

scanning said sensor from one side of the test piece to the other with a determined travel speed across the test piece for each scan up to a determined distance from the expected position of said edge, at which position the speed of the device is lowered to a level considerably lower than said travel speed, so that said device passes said edge at the lower speed.

* * * * *